United States Patent [19]

Doerfel

[11] Patent Number: 6,114,702
[45] Date of Patent: Sep. 5, 2000

[54] GAMMA CAMERA

[75] Inventor: Hans Doerfel, Kandel, Germany

[73] Assignee: Forschungszentrum Karlsruhe GmbH, Karlsruhe, Germany

[21] Appl. No.: 09/106,159

[22] Filed: Jun. 29, 1998

Related U.S. Application Data

[63] Continuation-in-part of application No. PCT/EP97/00124, Jan. 13, 1997.

[30] Foreign Application Priority Data

Jan. 30, 1996 [DE] Germany ............................ 196 03 212
Jan. 13, 1997 [EP] European Pat. Off. .. PCT/EP97/00124

[51] Int. Cl.[7] .............................. G01T 1/164; G01P 1/202
[52] U.S. Cl. ............................................ 250/366; 250/369
[58] Field of Search ........................ 250/363.01, 363.02, 250/363.1, 366, 370.11, 369, 361 R

[56] References Cited

U.S. PATENT DOCUMENTS

| 3,854,047 | 12/1974 | Suhami et al. ........................... 250/366 |
| 3,855,473 | 12/1974 | Burgess et al. . |
| 4,010,373 | 3/1977 | Kay . |
| 4,348,591 | 9/1982 | Wunderlich . |
| 5,077,479 | 12/1991 | de la Barre et al. ................. 250/363.1 |
| 5,317,158 | 5/1994 | McElhinney et al. . |
| 5,557,107 | 9/1996 | Carcreff et al. ...................... 250/361 R |

*Primary Examiner*—Constantine Hannaher
*Assistant Examiner*—Albert Gagliardi
*Attorney, Agent, or Firm*—Klaus J. Bach

[57] ABSTRACT

In a gamma camera comprising a hollow-body scintillator crystal which is open at one end and has optoelectronic transducers disposed at its outer surface for sensing light signals generated by gamma radiation entering the scintillator crystal, a collimator with a pin hole is disposed at the open end of the scintillator crystal and has a cone-like projection with an apex where the pin hole is disposed. A number of such hollow scintillator crystals may be arranged on sheets with cone-like projections having pin hole apexes so as to be coaxial with the pin holes.

5 Claims, 3 Drawing Sheets

GAMMA CAMERA

This is a continuation-in-part application of international application PCT/EP97/00124 filed Jan. 13, 1997 and claiming the priority of German application No. 196 03 212.1 filed Jan. 3, 1996.

BACKGROUND OF THE INVENTION

The invention relates to a gamma camera comprising a scintillator crystal with a pinhole collimator, at least four optoelectronic transducers with amplifiers and an evaluation unit.

Such a camera is known for example from Hermann, H. J. Nuklearmedizin, publisher: Urban & Schwarzenberg, Munich, 3rd edition 1992.

Gamma cameras known in the art consist generally of a large area NaI(Tl)-crystal provided at its front side with a collimator and, at its backside, with an arrangement of up to 90 photomultipliers. The sensitivity and the spatial resolution capability are determined mainly by the area of the NaI(Tl)-crystal and the structure of the collimator. The best spatial resolution capability is obtained, at this time, with so-called pin hole collimators with small opening diameters; however, the sensitivity of such a camera is relatively low. To increase the sensitivity, it is possible to use several cameras simultaneously. However, because of the relatively large dimensions of the cameras, the space limits are rapidly reached.

U.S. Pat. No. 3,855,473 discloses scintillator crystals with upwardly widening collimators, optoelectronic transducers including amplifiers and an evaluation unit wherein the scintillators are hollow bodies which are open at one side. However, they do not provide for a high spatial resolution.

In addition, U.S. Pat. No. 4,348,591 discloses a gamma camera of the type referred to above which, however, has a very small field of vision because the pinhole collimator has the shape of a recessed structure.

SUMMARY OF THE INVENTION

In a gamma camera comprising a hollow-body scintillator crystal which is open at one end and has optoelectronic transducers disposed at its outer surface for sensing light signals generated by gamma radiation entering the scintillator crystal, a collimator with a pin hole is disposed at the open end of the scintillator crystal and has a cone-like projection with an apex where the pin hole is disposed. A number of such hollow scintillator crystals may be arranged on sheets with cone-like projections having pin hole apexes so as to be coaxial with the pin holes.

Compared to state-of-the-art pinhole cameras, the gamma camera with a hollow body crystal and a pinhole collimator provides for a large field of vision, a smaller measuring distance and, in connection therewith, an improved sensitivity. With the compact design achieved by the invention, several pin hole cameras can be easily combined to a highly sensitive array with which also three dimensional representations of the activity distribution in the object to be measured can be generated. The advantage over an arrangement of several cameras utilizing the normal pinhole collimator technique is that, depending on the number of the hollow crystal cameras used, larger impulse rates can be processed and that, with a comparable spatial resolution capability, a higher sensitivity is achieved. This is particularly advantageous for dynamic examinations. The advantage regarding SPECT resides in the fact that the tomography can be performed with a stable geometry. This is also very advantageous in connection with dynamic examinations.

An embodiment of the invention will be described below on the basis of the accompanying drawings:

DESCRIPTION OF A PREFERRED EMBODIMENT

Figure 1:
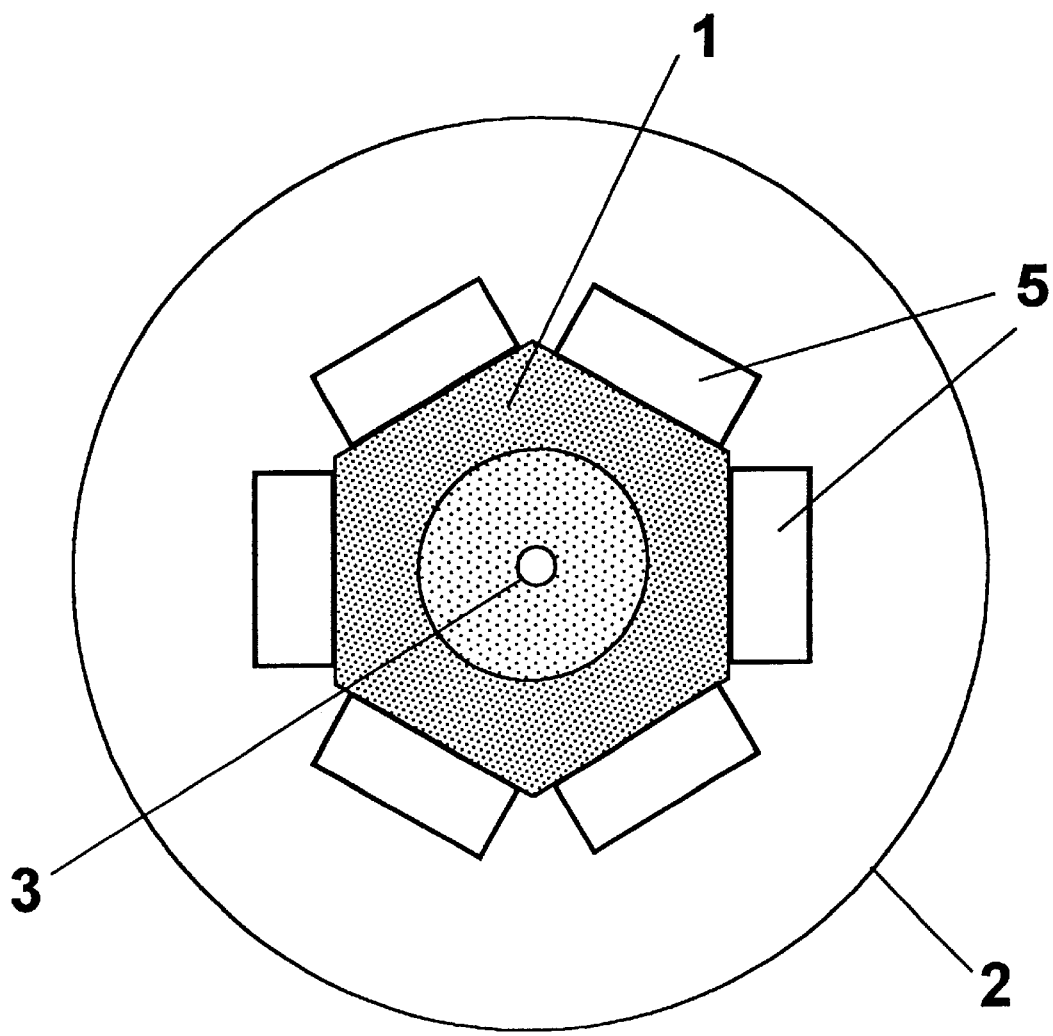
FIG. 1 shows the camera schematically in a cross-sectional view taken in a plane normal to the longitudinal axis of the crystal cavity.

FIG. 1 shows, as core of the camera, a cylindrical hollow body crystal 1 whose outer circumference is ground to be hexagonal. The hollow body crystal may consist of any substance which can be excited by radioactive radiation to emit light for example NaI(Tl) and CsI(Tl).

The hollow body 1 has, depending on the desired field of vision and the desired spatial resolution, a diameter of about 2 cm to about 15 cm and a depth of about 2 cm to about 30 cm. The wall thickness of the hollow body crystal is as small as it is technically possible to make it (at least about 1 cm).

On the ground, outer faces of the crystal 1, there are six optoelectronic transducers 5. The collimator 2 and the diaphragm 3 are shown as circles. The number of outer facets can be between 4 and 10.

Figure 2:
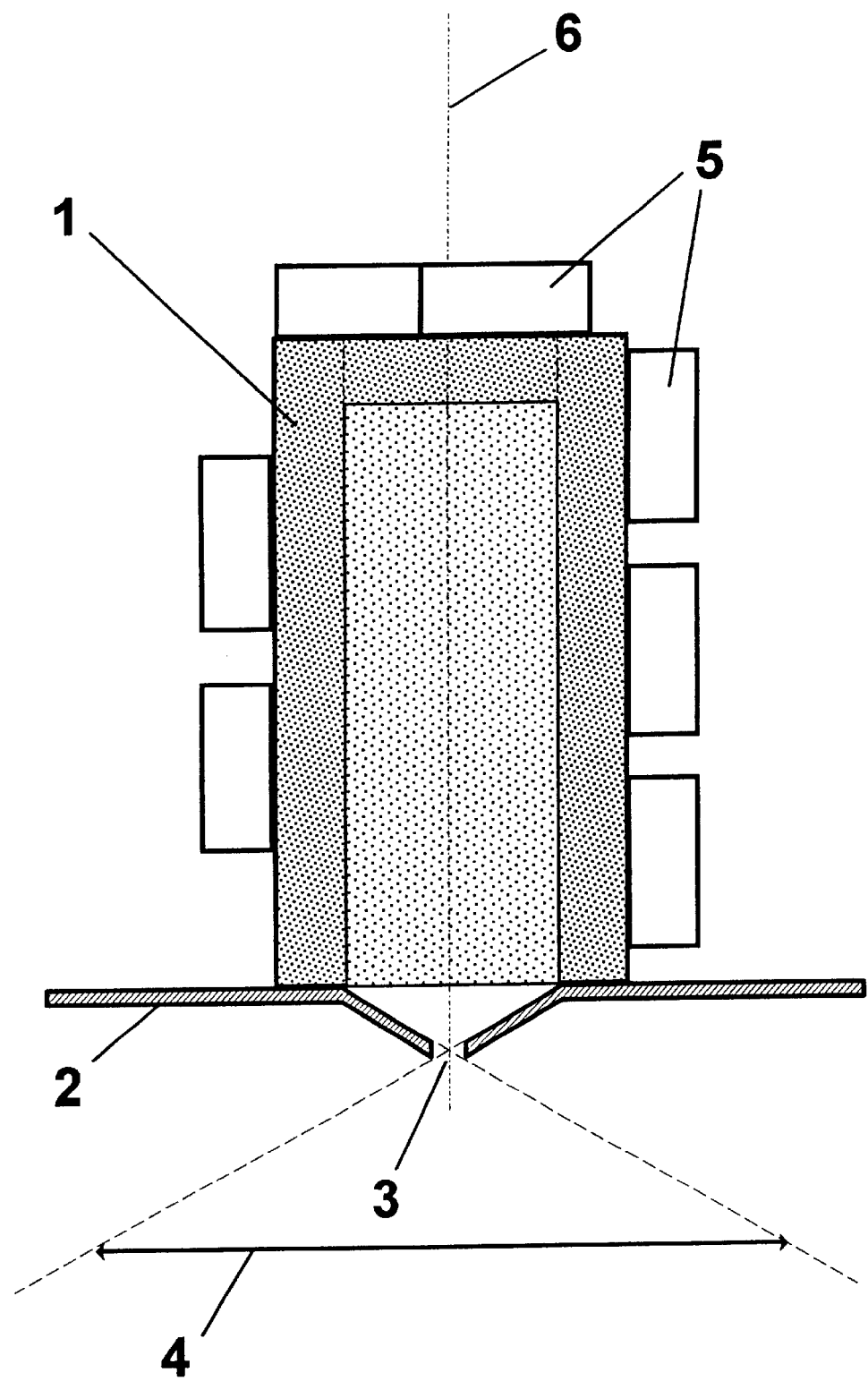
FIG. 2 shows schematically an axial cross-section.

FIG. 2 shows, disposed on the crystal 1, which has a U-shaped cross-section, alternately two and, respectively three optoelectronic transducers 5 (only two being shown), which are arranged in axial symmetry above those crystal segments on whose outer wall only two optoelectronic transducers are disposed. In this way, almost all the points in the crystal volume are covered by two photomultipliers. With relatively long crystals, correspondingly more optoelectronic transducers should of course be provided. The arrow 4 marks the opening angle of the field of view.

Downwardly, the crystal is closed by a pinhole collimator 2, which has a cone-like shape in the area of the body cavity. In the center of the collimator, there is a diaphragm 3 with an opening having a diameter which, dependent on the desired spatial resolution, is between about 1 mm and 5 mm. The field of vision has, depending on the shape of the collimator 2, an opening angle up to about 120°.

The radiation incidence direction is determined by a straight line defined by the location of the scintillation and the center point of the collimator diaphragm just like in the present pinhole cameras. The determination of the scintillation location occurs by a comparison of the light intensities recorded by the various photomultipliers. With the present arrangement, a three dimensional determination of the scintillation location can be obtained—in contrast to the prior art pinhole cameras. This provides for a substantially improved determination of the radiation incidence direction particularly with large incidence angles.

With the gamma camera described herein, two-dimensional pictures can be produced like with the state-of-the-art pin hole cameras by projecting the measured directional distribution of the incident radiation into a predetermined object plane. The picture quality is better the shorter the average distance nuclide deposition is from this projection plane.

With an array of several hollow crystal cameras, in addition, three dimensional representations of the activity distribution can be generated by unfolding the directional distributions measured by the various cameras in a way similar to the 7 segment pin hole collimator technique or the single photon emission computer tomography (Hermann, H. J., Nuklearmedizin, Publisher Urban & Schwarzenberg, Munich, Third Edition, 1992, pages 64–66 respectively, pages 55–58).

Figure 3:
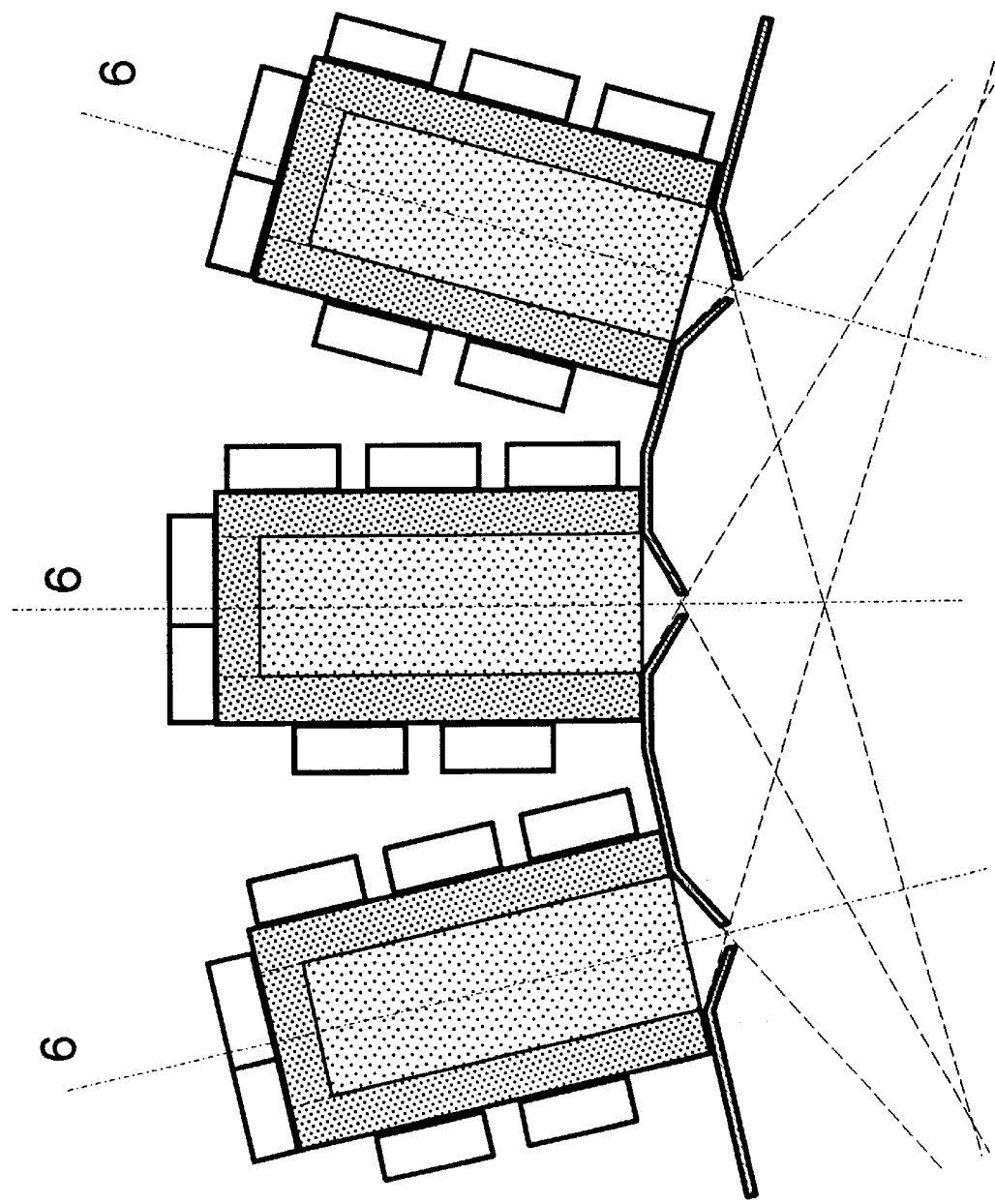
FIG. 3 shows a system comprising several cameras.

FIG. 3 shows a photon emission computer tomography system, in which six additional peripheral cameras are arranged radially around a central camera. The symmetry axes 6 of the six peripheral cameras extend at an angle to the symmetry axis of the central camera so that a large-area overlap of the fields of vision of the various cameras is obtained. The cavities of the crystals 1 have in this example a diameter of about 6 cm and a depth of about 15 cm. The tomography system consequently has at a measuring distance of 15 cm a viewing area of about a 60 cm diameter.

As optoelectronic transducer photomultipliers or thin photodiodes may be used for the recording of the scintillation light. With the use of the latter, it is advisable to use CsI(T1) crystals, since the spectral distribution of the scintillation light with this with this material is better suitable for the spectral response capability of the photodiodes.

With the use of photodiodes, the arrangement becomes even more compact so that, in principle, even more camera modules can be combined to a tomography system. However, the noise-signal-distance of the presently available photodiodes is smaller than that of photomultipliers so that the gain with regard to spatial resolution and sensitivity cannot yet be evaluated.

What is claimed is:

1. A gamma camera comprising a hollow body scintillator crystal, which is open at one end, at least four optoelectronic transducers with amplifiers arranged around said scintillator crystal, and a collimator with a pin hole disposed on said scintillator crystal so as to extend across said open end thereof, said collimator including a cone-like projection having an apex and said pin hole being disposed at said apex.

2. A gamma camera according to claim 1, wherein said hollow body is a cylinder with a concentric cylindrical bore hole.

3. A gamma camera according to claim 2, wherein said cylinder has flat outer surface sections.

4. A gamma camera according to claim 1, wherein said hollow body consists of plane-parallel segments.

5. An arrangement including a number of gamma cameras arranged adjacent one another on a collimator plate having spaced conical projections with pin holes formed at the apexes of the projections and scintillator crystals having cylindrical cavities with front openings disposed on said collimator plate coaxially with said pin holes, and optoelectronic transducers disposed on the outside of said scintillator crystals for sensing light signals generated by γ radiation entering said crystals through said pin holes.

* * * * *